(12) United States Patent
Blakemore et al.

(10) Patent No.: US 8,940,046 B2
(45) Date of Patent: Jan. 27, 2015

(54) METHOD OF IMPLANTING A PROSTHESIS DEVICE USING BONE CEMENT IN LIQUID FORM

(75) Inventors: David Blakemore, Warsaw, IN (US); Keith Pennington, Warsaw, IN (US); Shaun Pitts, Warsaw, IN (US)

(73) Assignee: Maxx Orthopedics, Inc., Plymouth Meeting, PA (US)

( * ) Notice: Subject to any disclaimer, the term of this patent is extended or adjusted under 35 U.S.C. 154(b) by 234 days.

(21) Appl. No.: 13/249,044

(22) Filed: Sep. 29, 2011

(65) Prior Publication Data

US 2012/0083789 A1 Apr. 5, 2012

Related U.S. Application Data

(60) Provisional application No. 61/389,193, filed on Oct. 1, 2010.

(51) Int. Cl.
*A61F 2/28* (2006.01)
*A61B 17/88* (2006.01)
*A61B 19/00* (2006.01)
(Continued)

(52) U.S. Cl.
CPC ......... *A61B 17/8836* (2013.01); *A61B 17/8827* (2013.01); *A61B 17/8833* (2013.01); *A61B 17/8811* (2013.01); *A61B 19/46* (2013.01); *A61B 2017/8838* (2013.01); *A61F 2/32* (2013.01); *A61F 2/38* (2013.01); *A61F 2/3804* (2013.01); *A61F 2/3877* (2013.01); *A61F 2/40* (2013.01); *A61F 2/4202* (2013.01); *A61F 2/44* (2013.01); *A61F 2002/3895* (2013.01); *A61F 2002/4631* (2013.01)
USPC ................. 623/16.11; 623/23.62; 623/23.37; 606/92; 606/93

(58) Field of Classification Search
USPC ..................... 623/22.39, 23.29, 23.37, 23.62
See application file for complete search history.

(56) References Cited

U.S. PATENT DOCUMENTS

| 4,093,576 A | 6/1978 | deWijn |
| 4,341,691 A | 7/1982 | Anuta |

(Continued)

OTHER PUBLICATIONS

Baroud et al., "Injection Biomechanics of Bone Cements used in Vertebroplasty," *Journal Bio-Medical Materials and Engineering*, 14:487-504 (2004) (Abstract only).

(Continued)

*Primary Examiner* — Bruce E Snow
*Assistant Examiner* — Brian Dukert
(74) *Attorney, Agent, or Firm* — Heslin Rothenberg Farley & Mesiti P.C.

(57) ABSTRACT

The present invention relates to a method of implanting a prosthesis device in a subject. In one embodiment, this method involves: (i) providing a prosthesis device to be attached to an exposed surface of a bone; (ii) applying bone cement in liquid form to a bone-implant interface region, the bone-implant interface region including a region between the exposed surface of the bone and an outer surface of the prosthesis device; and (iii) contacting the bone cement to the exposed surface of the bone and the outer surface of the prosthesis device under conditions effective to allow the bone cement to cure, thereby resulting in attachment of the prosthesis device to the bone of the subject. The present invention also relates to a kit for implanting a prosthesis device in a subject, a method of performing a joint arthroplasty surgical procedure, and other methods of using bone cement in liquid form.

25 Claims, 10 Drawing Sheets

(51) Int. Cl.
  A61F 2/32    (2006.01)
  A61F 2/38    (2006.01)
  A61F 2/40    (2006.01)
  A61F 2/42    (2006.01)
  A61F 2/44    (2006.01)
  A61F 2/46    (2006.01)

(56) References Cited

U.S. PATENT DOCUMENTS

| | | | |
|---|---|---|---|
| 5,171,276 | A | 12/1992 | Caspari et al. |
| 5,336,266 | A | 8/1994 | Caspari et al. |
| 5,501,687 | A | 3/1996 | Willert et al. |
| 7,559,932 | B2 | 7/2009 | Truckai et al. |
| 2005/0137708 | A1 | 6/2005 | Clark |
| 2007/0032876 | A1 | 2/2007 | Clark |
| 2008/0188858 | A1* | 8/2008 | Luzzi et al. ............... 606/94 |
| 2009/0228112 | A1* | 9/2009 | Clark et al. ............ 623/20.32 |
| 2009/0228114 | A1 | 9/2009 | Clark et al. |

OTHER PUBLICATIONS

Chavali et al., "Extending Polymerization Time of Polymethylmethacrylate Cement in Percutaneous Vertebroplasty with Ice Bath Cooling," *American Journal of Neuroradiology*, 24:545-546 (2003).

Farrar et al., "Rheological Properties of PMMA Bone Cements During Curing," *Biomaterials*, 22(22):3005-3013 (2001) (Abstract only).

Gisep et al., "Augmentation of Implant Purchase with Bone Cements: An In Vitro Study of Injectability and Dough Distribution," *Journal of Biomedical Materials Research*, 77B(1):114-119 (2005) (Abstract only).

Junaid et al., "Failure Mechanism of the All-Polyethylene Glenoid Implant," *Journal of Biomechanics*, 43:714-719 (2010).

Krause et al., "Strength of the Cement-Bone Interface," *Clinical Orthopaedics and Related Research*, 163:290-299 (1982).

Kuehn et al., "Acrylic Bone Cements: Composition and Properties," *Orthopedic Clinics of North America*, 36(1):17-28 (2005) (Abstract only).

Lidgren et al., "Bone Cement Improved by Vacuum Mixing and Chilling," *Acta Orthop. Scand.*, 57:27-32 (1987).

Loeffel et al., "Vertebroplasty: Experimental Characterization of Polymethylmethacrylate Bone Cement Spreading as a Function of Viscosity, Bone Porosity, and Flow Rate," *Spine*, 33(12):1352-1359 (2008) (Abstract only).

Parks et al., "Effect of Increasing Temperature on the Properties of Four Bone Cements," *Clinical Orthopaedics and Related Research*, 355:238-248 (1998).

Sullivan et al, "Influence of Initial Component Temperature on the Apparent Viscosity and Handling Characteristics of Acrylic (PMMA) Bone Cement," *Journal of Biomedical Materials Research*, 81B(1):224-230 (2006) (Abstract only).

* cited by examiner

METHOD OF IMPLANTING A PROSTHESIS DEVICE USING BONE CEMENT IN LIQUID FORM

CROSS-REFERENCE TO RELATED APPLICATIONS

This application claims priority benefit of U.S. Provisional Patent Application Ser. No. 61/389,193, filed Oct. 1, 2010, the disclosure of which is hereby incorporated by reference herein in its entirety.

FIELD OF THE INVENTION

The present invention generally relates to the use of bone cement in a liquid form in joint arthroplasty.

BACKGROUND OF THE INVENTION

During the resurfacing techniques used in joint arthroplasty, the boney surface is prepared using saw cuts, mills or burs, and a metal or plastic insert is bonded to the prepared surface of the bone using a bone cement such as poly methyl methacrylate (PMMA) in a paste or dough form. The bone cement is applied to the surface of the resected bone, the underside of the implant, or both and the implant is put in place. The bone cement is in the form of a thick bonding agent that is easily handled since it can be kneaded into shape and pressed into place by hand. At the stage it is used it also does not stick to the surgeons tools or gloves which makes it even easier to handle. However, there are significant limitations in using such bone cement for joint arthroplasty. For example, it is difficult to insert the bone cement into narrow or tight spaces in and around the implant area. Further, the bone cement is not easily conformable to complex geometries. Less viscous forms of the bone cement also are problematic because they can leak or have unreasonable curing times, leading to ineffective or poorly setting implants. In addition, this sort of thinner bone cement is difficult to contain and adheres to most surfaces it comes in contact with, making it difficult for surgical teams to use in joint arthroplasty procedures.

There is a need for a method for using bone cement in a liquid form in joint arthroplasty, where the bone cement is less viscous (e.g., in a liquid cement form) than the traditional bone cement currently and regularly used in the art. There is also a need for a bone cement that has the ability to fill the bone voids more readily and provide better adhesive properties as it is applied to joint arthroplasty.

The present invention is directed to overcoming these and other deficiencies in the art.

SUMMARY OF THE INVENTION

In one aspect, the present invention relates to a method of implanting a prosthesis device in a subject. This method involves the following steps: (i) providing a prosthesis device to be attached to an exposed surface of a bone of a subject; (ii) applying bone cement in liquid form to a bone-implant interface region, where the bone-implant interface region includes a region between the exposed surface of the bone and an outer surface of the prosthesis device; and (iii) contacting the bone cement to both the exposed surface of the bone and the outer surface of the prosthesis device under conditions effective to allow the bone cement to cure, thereby resulting in attachment of the prosthesis device to the bone of the subject.

In another aspect, the present invention relates to a kit for implanting a prosthesis device in a subject. The kit includes: (i) a prosthesis device comprising a body having at least one port through which bone cement in liquid form can be applied to a bone-implant interface region, where the bone-implant interface region includes a region between an exposed surface of a bone of the subject and an outer surface of the prosthesis device; and (ii) a user manual comprising instructions for applying bone cement in liquid form to said bone-implant interface region.

In another aspect, the present invention relates to a method of performing a joint arthroplasty surgical procedure. This method involves the following steps: (i) providing a prosthesis device for use in a joint arthroplasty surgical procedure and to be attached to an exposed surface of a bone of a subject, where the prosthesis device includes at least one portal; and (ii) directing bone cement in liquid form through the at least one portal to a bone-implant interface region, where the bone-implant interface region includes a region between the exposed surface of the bone and an outer surface of the prosthesis device, thereby resulting in attachment of the prosthesis device to the bone of the subject.

In a further aspect, the present invention relates to a method of reattaching loose implants arthroscopically using bone cement in liquid form, as described herein.

In another aspect, the present invention relates to a method of performing a bone-to-bone fusion using bone cement in liquid form, as described herein.

The present invention provides a method of joint arthroplasty that involves using a less viscous or liquid cement than is the traditional bone cement currently used in the art. The present invention provides a bone cement having the ability to fill the bone voids more readily and therefore provide a stronger attachment to the bone. Further, the present invention provides a technique to apply low viscosity cement to the needed area.

The present invention provides a technique to apply a low viscosity cement to the needed area. The use of the bone cement (e.g., PMMA) in this form is typically discouraged since it is difficult to handle in the surgical setting. However, the present invention solves the issues of handling the low viscosity bone cement by providing a system that includes the choice of cement, mixing, transfer, effects of environmental factors, stages and application of a liquid cement in a way that benefits the patient and the surgeon.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

DETAILED DESCRIPTION OF THE INVENTION

Figure 1:
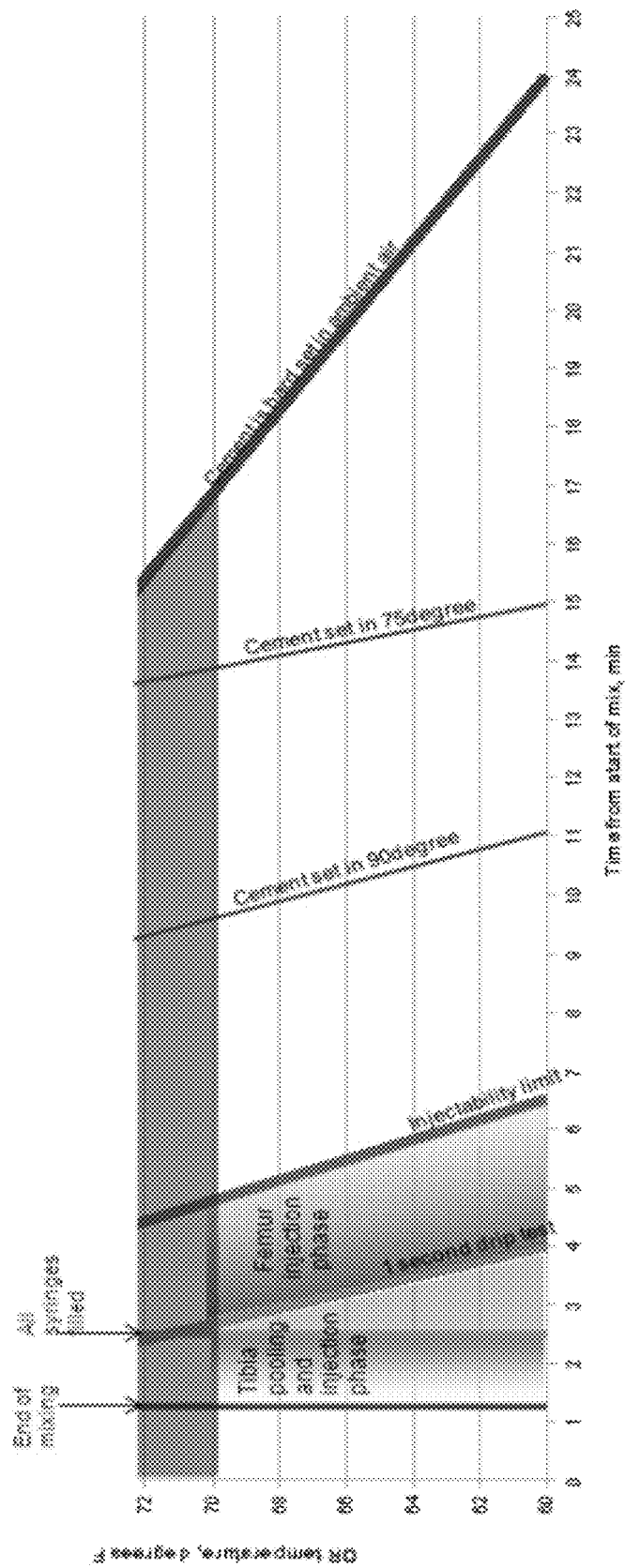
FIG. 1 is a graph chart showing bone cement properties for Palacos LV cement, including set times and injectability ranges.

The present invention provides a method of implanting a prosthesis device in a subject. This method involves the following steps: (i) providing a prosthesis device to be attached to an exposed surface of a bone of a subject; (ii) applying bone cement in liquid form to a bone-implant interface region, where the bone-implant interface region includes a region between the exposed surface of the bone and an outer surface of the prosthesis device; and (iii) contacting the bone cement to both the exposed surface of the bone and the outer surface of the prosthesis device under conditions effective to allow the bone cement to cure, thereby resulting in attachment of the prosthesis device to the bone of the subject.

The method of the present invention is suitable for use with all types of prosthesis devices. For example, a suitable prosthesis device can include, without limitation, a joint prosthesis device for replacing or partially replacing a joint such as a knee, a hip, a shoulder, an ankle, an elbow, a spinal disc, a cervical disc, and a small joint. Other suitable examples of prosthesis devices for use in the method of the present invention can include, without limitation, devices having all or portions of a tibial component, a femoral component, a patellar component, an acetabular component, a glenoid component, a humeral component, a talar component, an ulnar component, or a fusion cage component. In one embodiment, the prosthesis device can include a body having at least one port through which the bone cement in liquid form is applied to the bone-implant interface region.

Other suitable examples of joint prosthesis devices can be those used for a partial knee replacement, a patello-femoral replacement, or a total knee replacement. With regard to joint prosthesis devices for small joints, suitable devices can be those used for a PIP joint (finger), an MCP joint (knuckle), a DIP joint (finger), a CMC joint (thumb), and a metatarsophalangeal joint (toe).

Various types of bone cement known in the art can be used in the methods of the present invention, as long as such bone cement is configured to be in liquid form in accordance with the present invention. In one embodiment, the bone cement in liquid form can be, without limitation, poly(methyl methacrylate) (PMMA) at a viscosity of about 10,000 centipoise (cP) or less, about 9,000 cP or less, about 8,000 cP or less, about 7,000 cP or less, about 5,000 cP or less, about 4,000 cP or less, about 3,000 cP or less, about 2,500 cP or less, about 2000 cP or less, about 1500 cP or less, about 1000 cP or less, about 500 cP or less, about 250 cP or less, and the like.

In one embodiment of the method of the present invention, the applying step includes introducing the bone cement in liquid form to the bone-implant interface region through at least one port of the prosthesis device.

In another embodiment of the method of the present invention, prior to the applying step, the method further includes conducting a viscosity test on the bone cement to determine a viscosity range at which the bone cement is in liquid form suitable for applying to the bone-implant interface region.

A suitable viscosity test for use in the present invention can include, without limitation, a drip test effective to measure the rate of flow, where the viscosity test is suitable to provide a beginning and ending point for applying the bone cement in liquid form. In one embodiment, for example, the beginning point can be a rate of flow such as 2 drips/second, 1 drip/second, and 1 drip/5 seconds, and the like. In another embodiment, for example, the ending point can be a rate of flow such as less than about 1 drip/5 seconds, less than about 1 drip/10 seconds, and no apparent drips/5-10 seconds.

Another suitable viscosity test for use in the present invention can include, without limitation, a test that involves measuring migration of the bone cement on a test surface under conditions effective to determine when the bone cement is in a liquid form having a suitable viscosity range for said applying step.

Yet another suitable viscosity test for use in the present invention can include, without limitation, a test that involves measuring the change in temperature of the bone cement under conditions effective to determine when the bone cement is in a liquid form having a suitable viscosity range for said applying step.

In another embodiment of the method of the present invention, after the applying step and/or after the contacting step, the method further includes subjecting the bone cement to curing conditions effective to decrease the setting time of the implanted prosthesis device. In a particular embodiment, the subjecting can include, without limitation, adding heat to the bone cement. As a suitable example, the heat can be added using saline at a temperature of between about 80 and 100 degrees F.

Various means for applying the bone cement in liquid form in accordance with the methods of the present invention can be used. For example, in one embodiment, the bone cement in liquid form is applied to the bone-implant interface region using a delivery instrument. Those of ordinary skill in the art, in view of the present specification, can determine various types of delivery instruments that are suitable for use in the methods of the present invention. A syringe is a suitable example of a delivery instrument for use in the method of the present invention. Those of ordinary skill in the art can readily determine the various types and sizes of syringes that can be used in the methods of the present invention. While not intending to be limiting, in a particular example, the syringe can be configured to contain a volume of liquid of up to about 50 cubic centimeters (cc).

In one embodiment, an injector adapter is used to facilitate application of the bone cement in liquid form from the delivery instrument to the bone-implant interface region. In a particular embodiment, the prosthesis device includes a body having at least one port through which the bone cement in liquid form is applied to the bone-implant interface region, with the injector adapter being configured to couple the injection instrument to the at least one port of the prosthesis device.

In another embodiment of the method of the present invention, prior to and/or during the applying step, the method further includes delaying curing of the bone cement from its liquid form to its cured form. In a particular embodiment, this delaying step can include maintaining the bone cement in liquid form at a temperature range such as, but not limited to, a temperature range of between about 0° F. and about 40° F., between about 10° F. and about 40° F., between about 15° F. and about 40° F., between about 20° F. and about 40° F., between about 25° F. and about 40° F., between about 30° F. and about 38° F., between about 32° F. and about 35° F., and the like. In another particular embodiment, this delaying step includes maintaining the bone cement at a temperature of not more than about 0° F. Those of ordinary skill in the art, in view of the specification, would readily understand how to achieve the delaying step. While not intending to be limiting, in a particular example, the delaying step can include maintaining the bone cement in crushed ice, a mixture of ice and water, refrigerator-chilled saline, and/or freezer-chilled saline.

Suitable means for carrying out the maintaining step can include, for example, incubating the bone cement in liquid form in an ice bath or chilling the bone cement in liquid form using chilled saline. In a particular embodiment, the incubating is for a period of not more than about 25 minutes and/or not more than between about 10 and about 25 minutes prior to applying the bone cement in liquid form to the bone-implant interface region.

The present invention also provides a kit for implanting a prosthesis device in a subject. The kit includes: (i) a prosthesis device comprising a body having at least one port through which bone cement in liquid form can be applied to a bone-implant interface region, where the bone-implant interface region includes a region between an exposed surface of a bone of the subject and an outer surface of the prosthesis device; and (ii) a user manual comprising instructions for applying bone cement in liquid form to said bone-implant interface region.

The kit of the present invention can further include an injection instrument for applying the bone cement in liquid form through the at least one port of the prosthesis device. Suitable examples of injection instruments are as disclosed herein and as readily understood by those of ordinary skill in the art in view of the present specification. The kit of the present invention can further include an injector adapter configured to couple the injection instrument to the at least one port of the prosthesis device.

The present invention further provides a method of performing a joint arthroplasty surgical procedure. This method involves the following steps: (i) providing a prosthesis device for use in a joint arthroplasty surgical procedure and to be attached to an exposed surface of a bone of a subject, where the prosthesis device includes at least one portal; and (ii) directing bone cement in liquid form through the at least one portal to a bone-implant interface region, where the bone-implant interface region includes a region between the exposed surface of the bone and an outer surface of the prosthesis device, thereby resulting in attachment of the prosthesis device to the bone of the subject.

The present invention also provides a method of reattaching loose implants arthroscopically using bone cement in liquid form, as described herein. Those of ordinary skill in the art, in view of the present specification, can readily determine the steps involved in perform this method.

The present invention further provides a method of performing a bone-to-bone fusion using bone cement in liquid form, as described herein. Those of ordinary skill in the art, in view of the present specification, can readily determine the steps involved in perform this method.

Traditional bone cement (e.g., PMMA) used in joint arthroplasty is normally used in a doughy state. Manufacturers of traditional bone cement provide descriptions of the normal working phase: a doughy state that no longer sticks to a gloved hand. This state is accurately defined and predicted by existing ambient temperature charts. However, the manufacturers do not characterize "injectability" as it is done with respect to the present invention. Therefore, the information that bone cement manufacturers provide does not apply for application in a liquid state. What descriptions there are for using cement in a liquid state only apply to vertebroplasty and other vertebra augmentation procedures where the cement is injected with high pressure directly into the trabecular structure of the bone itself, not between implants and bone as would be relevant to joint replacement surgery. For example, the Caspari group describes a method of injecting liquid cement underneath the implant but not through the implant.

The present invention provides, inter alia, a method that involves the application of cement in a liquid state that is superior to "thumb-packing" a standard doughy-state cement because it greatly increases the interdigitation of the cement into the trabecular structure of the bone beneath the implant. This results in greater structural stability, which should in turn lead to fewer implant failures due to loosening—a leading cause of revision reoperations. By enabling the surgeon to confidently inject cement at a lower viscosity, the present invention helps to alleviate this and other problems relating to joint arthroplasty.

It is provided that a low viscosity cement would allow for a better mechanical bond to the trabecular structure of bone and the implant surface by providing greater interdigitation and penetration than the standard method of applying cement in a doughy state. It is also provided that this liquid form of the cement could provide for greater adhesive properties as seen in its properties at this stage seen in the inability to handle this liquid cement easily as it sticks to any surface it comes into contact with. It is further provided that liquid cement can be injected through small openings as opposed to a doughy cement which is applied to the surface to be bonded first and then the surfaces joined. In the present invention, the implants can be set in place and the cement injected in the space between the component and the host bone. Unlike the present invention, the prior art does not provide current guidelines for injecting cement through a syringe relevant for use in orthopedic arthroplasty.

The present invention, in one embodiment, provides two parts. The first part is the implant devices with which this liquid injection technique can be used with, and the second part is the application and methodology used to control the injectability of the cement. Some distinguishing characteristic of the implant devices to be used with this process is that they have portals that allow for an interface of a pressurization system and channels to direct the flow of the injected cement. A distinguishing characteristic of the injectable cement system is that it is used early in the mixing and curing process of the cement so that it is at a low viscosity upon application—and the application of the cement takes place when the implant is already in place. Specialized implant design and injecting instrumentation can be used along with cement in this state, which may otherwise be too thin to handle and utilize effectively.

Implants are developed with dams that limit extrusion and which also guide the flow. Special interlocking geometries on the under surfaces of implants are also developed to work with liquid cement—these geometries allow cement to flow into and up around corners of the implant in order to get a stronger mechanical lock. Injectors which attach to portals on the implant on one end and syringes on the other are developed for a simple cement injection protocol. These features and instruments are new to joint replacement implant techniques.

The present invention does not formulate a new kind of cement, but instead in one embodiment takes advantage of regularly available PMMA bone cement that is used at an earlier stage of the curing process. Cement applied with LiquiFlo technology of the present invention is chemically and structurally the same as the original commercial bone cement used as there is no addition or removal of any ingredients and there is no change of the chemical makeup of the cement in any way.

In one embodiment, this technique description of the present invention outlines the parameters needed to allow for an injectable cement to be used in the operating room. For example, it includes preparation, mixing, setting times and establishes injectability ranges for use within a surgical arthroplasty procedure utilizing PMMA cement in its liquid state.

Step 1: Mixing the Cement

The PMMA cement is vacuum mixed in a container according to the manufactures recommendations (30-60 seconds).

Step 2: Transfer of Mixed Cement to Injection Syringe

The mixed cement is transferred to an appropriate sized syringe through a transfer port or by pouring the liquid cement directly into the large open end of the syringe.

Step 3: Determination of Injectability of the Cement and Suspension of Cement Curing A drip test is performed in which a separate cement-filled syringe is held vertically and the rate at which the cement drips from the syringe tip is monitored. The remainder of the mixed cement can be optional set into an ice bath of sterile water at 32-35 degrees to suspend its state of viscosity for subsequent use.

Step 4: Cement Delivery or Injection

The syringe is attached to the implant via a proprietary adapter and the plunger is pressed until the prescribed amount of cement is delivered to the underside of the implants.

The injectability range of the cement is very important to identify: a new phase is defined in which cement can be consistently pushed through injectors while completely filling the necessary boney voids and the geometries of the implant used to attain ridged fixation.

Examples of set times and injectability ranges are shown for Palacos LV cement in the graph of FIG. 1.

Important factors that affect injectability and set time include: (i) times of injection after initial mix; (ii) ambient temperature; (iii) addition of or subtraction of heat on the loaded syringe for different lengths of time; and (iv) bolus (different setting volume/waiting volume) effects.

Mixes generally take around the same time to complete and syringes are filled immediately after (mixes were usually complete at 1:15 min after initial monomer-cement contact and transferred to syringes at 2:15).

Viscosity is used as a metric for determining another term—"injectability" which is defined as the cement's viscosity as being below a certain value that is both easy to inject out of a standard syringe and spread down the length of a femoral partial knee implant—more viscous and it would not fill the implant but instead form a ball near the site of injection that pushes the implant out of place. The viscosities for different temperatures and bolus sizes are given as a function of time from mix for incorporation into a surgical procedure. Higher temperatures lead to faster set times, but also lead to increased viscosity early on, which limits injectability. Ranges are given for stages of injectability for both tibial and femoral components, as well as final set times for different setting-environment temperatures.

A procedure called the "drip-test" is a method to determine the ideal time for injection. It corresponds to a viscosity of around 500 to 1000 centipoise, and is easy to reproduce in an operating room environment. The cement is considered injectable when 1 drip of curing cement per second comes from tip of a plunger-less 10 cc syringe when held upright.

Injectability

Viscosity was determined by the Hagen-Poiseuille equation, $$\Delta P = -\frac{8\mu L Q}{\pi r^4}$$

which shows relationship between pipe size (L, r), flow rate (Q), pressure difference ($\Delta P$), and viscosity ($\mu$) for non-turbulent flow through a pipe.

When modeled at the end of the luer syringe, this equation gives viscosity as a function of weight applied (to create pressure difference $\Delta P$) and velocity of plunger (to calculate flow rate Q). The final equation is reached when modeled at the end of a luer syringe and a force of 10 pounds is applied to the plunger of a 10 cc syringe to create the pressure differential. This is factored in to the $\mu$-0.0684/Vx equation.

Bone cement is considered "injectable" when the viscosity is below a level where the cement can be comfortably pushed from a syringe and fill the volume underneath the implant while not pushing the implant out of place.

Times are defined where injectability "ends" for different ambient temperatures with standard mix conditions. These are outlined on the graph below, for Palacos LV.

The cement working stages and setting set times are important to know because the surgeon is concerned with the length of time needed to hold the knee in place while the cement sets. It is important to note that most practicing surgeons are trained to hold the limb in position for as long as it takes the cement to cure. Under standard mixes and "thumb pack" technique this is typically 10-15 minutes. The standard of care relies on these times and a bolus of cement from the original mix being monitored for curing outside the wound. It has been found that this method may not be reliable since a bolus of cement cures at a different rate than a mantle of cement that is located between the implant and the host bone. If the cement does not set properly, it could lead to malpositioning or early cement failure. It is important to know setting times in all conditions so that company representatives in the room may answer any questions should complications arise.

Icing

Since the curing reaction is largely heat-dependent, cooling the cement slows the reaction. Placing the filled syringe into an ice-bath after filling would therefore be useful, specifically in warmer Operating Room temperatures where the injectability phase ends just over 4 minutes after mix, leaving little time for the procedure to be completed.

The addition of the ice bath: removes ambient temperature variability, controls reaction time, extends injectability range, and 32 degrees is easy to reproduce. This is a value-added simple step to incorporate into the procedure.

Icing was found to slow injectability for up to 15 minutes. After 15 minutes, the reaction has progressed enough to increase the rate of becoming more viscous to a point where it would cause significant changes to the injectability of the cement.

Cement is a self-curing polymer, it should be noted that the reaction can be slowed by icing but not stopped. Icing slows the reaction and maintains the injectability state of the cement when it entered the ice bath for up to 15 minutes. When the cement is removed from the ice the curing times are delayed and care should be taken to ensure full cure. With the addition of a warm water lavage after implantation, these delays are negligible.

Different holding volumes (before injection) were considered, as smaller boluses were previously shown to have longer set times. This was tested to determine if the holding bolus effects changed injectability. The results did not show any appreciable effect on injectability. Set times outlined here are for setting boluses of 2 cc each which is similar to the amount seen between the implant and the host bone for a partial knee replacement. Bolus effects had no noticeable effect on injectability, as a holding volume of 10 cc seemed to have the same injectability as 5 cc.

The surgical procedure for any arthroplasty using injecting liquid cement should include this information depicting the optimal time to inject the PMMA cement in order to ensure full cement fill underneath the implant and to minimize the amount of uncontrolled extrusion. The procedure should also outline the time required for the cement to cure sufficiently to avoid displacement of the implant while the final steps are performed.

One embodiment of a method of the present invention can include, for example, the below steps as contemplated during a surgical procedure and in a surgical setting for a partial knee procedure, as follows:

I. Pre-Surgery

If chilled saline is unavailable, prepare an ice bath before the procedure starts, and place a 1 liter sterile saline container within the ice bath. Chilled saline will be used later in the procedure to chill mixed cement. Ensure that 2 boxes of cements such as Palacos LV or Osteobond are available for surgery.

II. Pre-Cementing Steps

Pre-cementing steps can include, without limitation, the following steps:

1. After drilling three (3) 3.2 mm holes into the tibial plateau, lavage and dry area to remove bone and other debris that could prohibit free flow of cement and adhesion to the prepared bony surface.

2. Dry area with gauze or hydrosorb 4×4 and remove just before inserting implants into proper position.

Figure 2:
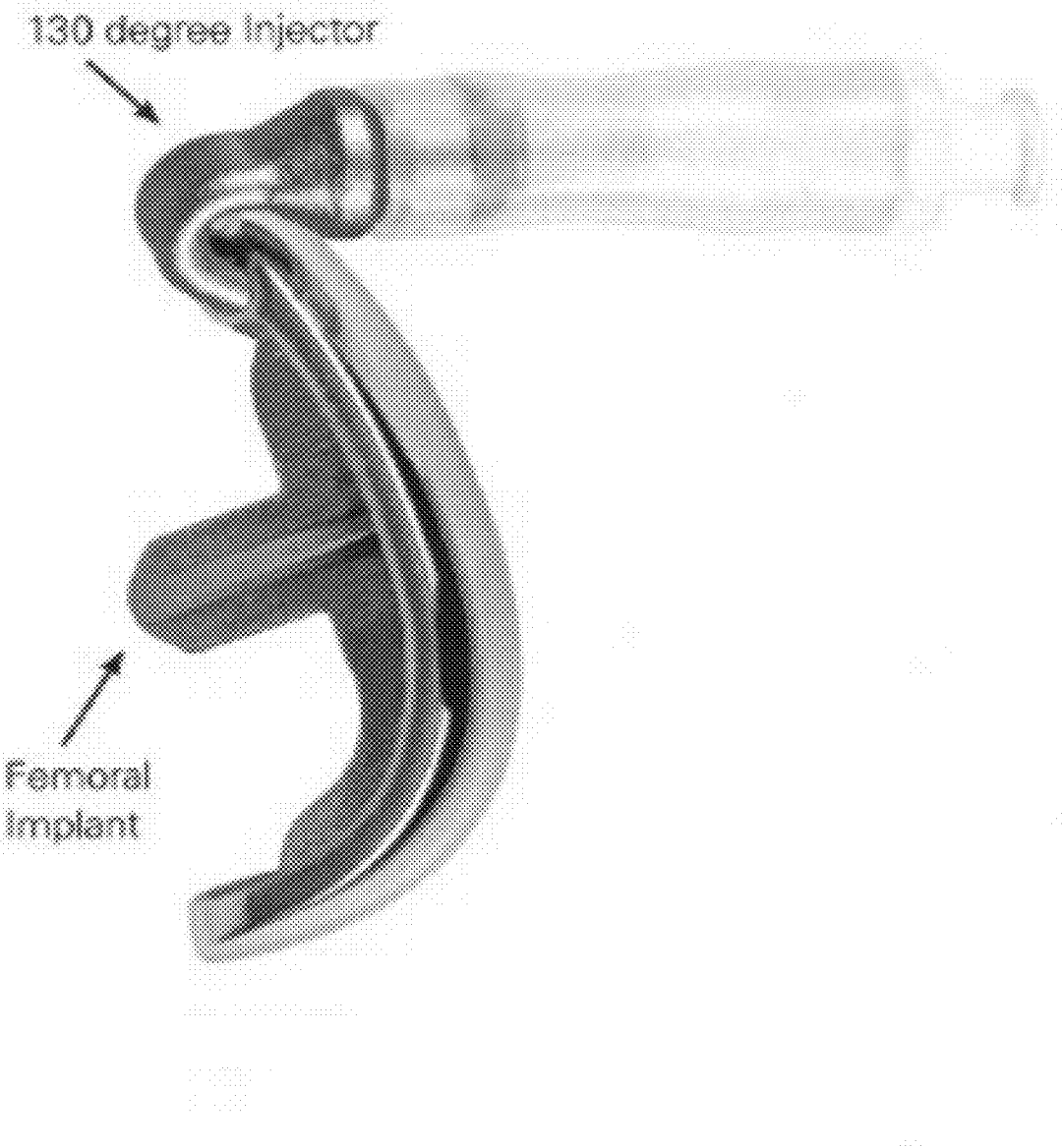
FIG. 2 is a photograph of a femoral implant and 130 degree injector used in one embodiment of a method of the present invention.
Figure 3:
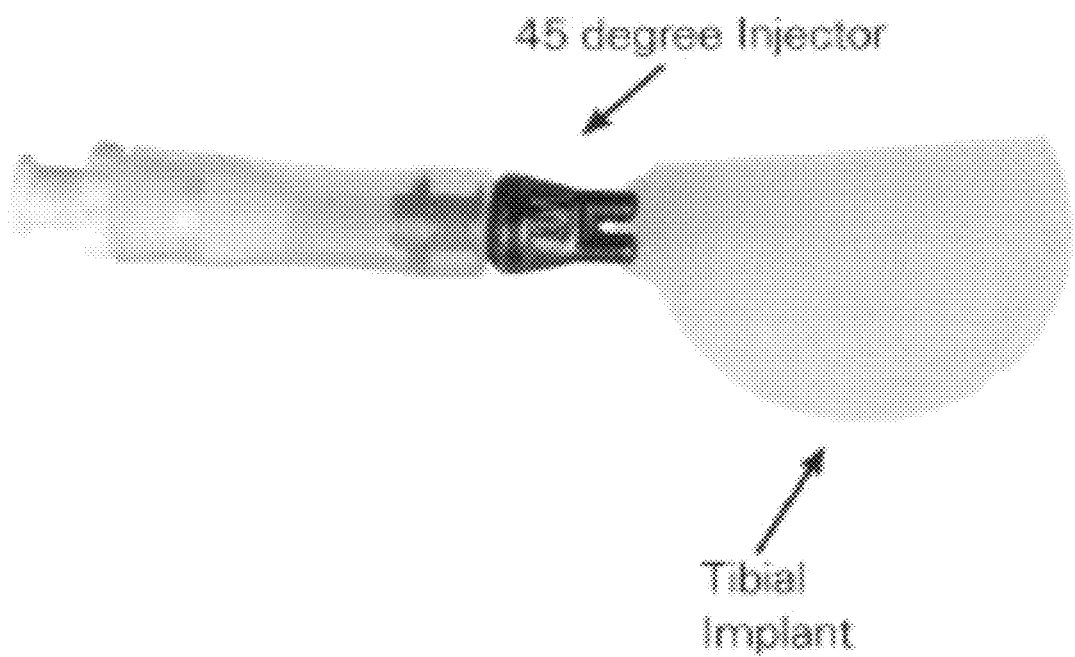
FIG. 3 is a photograph of a tibial implant and 45 degree injector used in one embodiment of a method of the present invention.

3. Place injector(s) in implants on back table to expedite cementing process (see FIG. 2 and FIG. 3).

4. Ensure surgeon is ready and has implants and injectors in place on back table prior to mixing.

5. Pour enough chilled saline into a container to completely cover cement-filled 10 mL syringe. Use needle cap to close end of syringe.

6. Have four (4) standard 10 mL syringes available for cementing technique.

III. Cement Mixing

Figure 4:
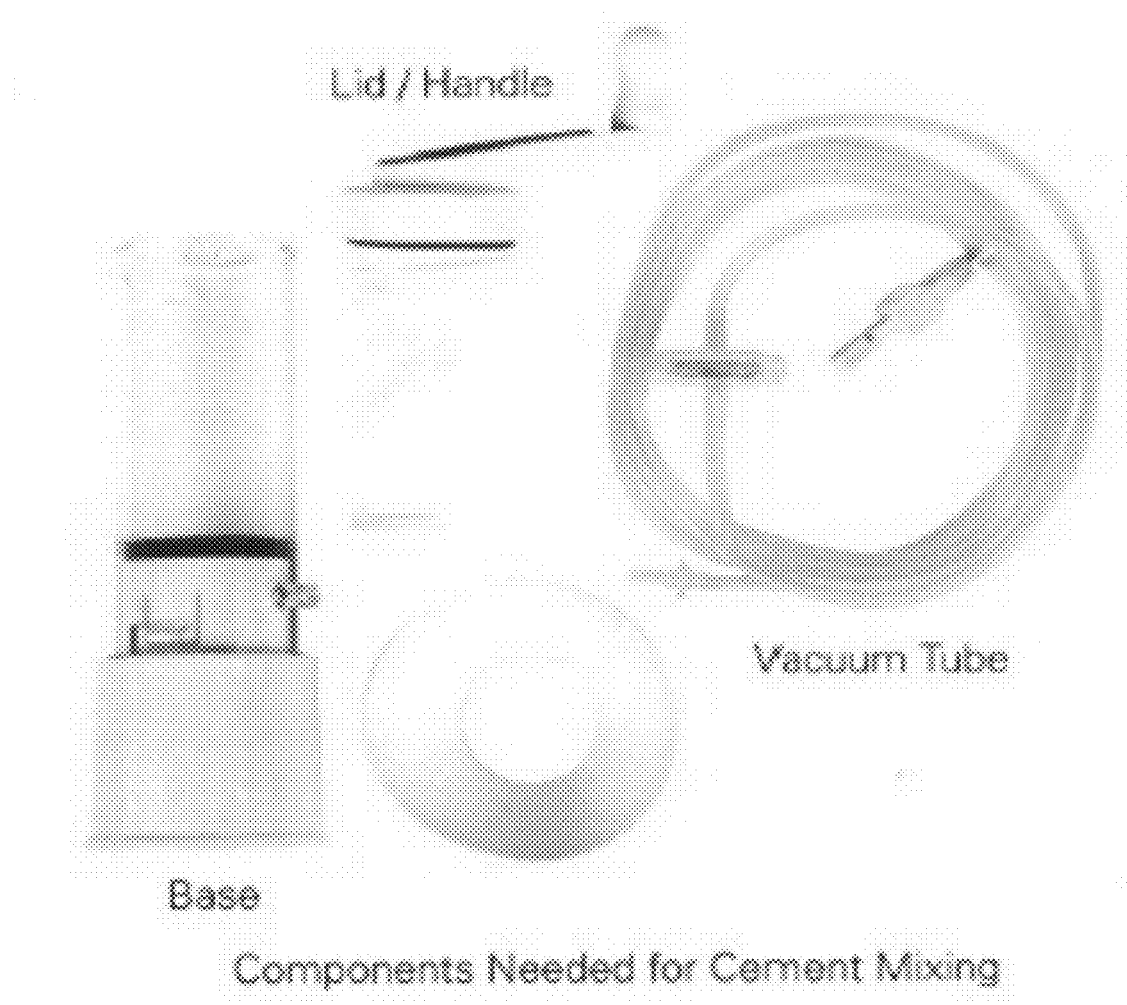
FIG. 4 is a photograph of various components used for cement mixing in one embodiment of a method of the present invention.

Cementing mixing steps can include, without limitation, the following steps:

1. Remove cement mixer and cement from any packaging. Examples of various components needed for cement mixing are shown in FIG. 4.

Figure 5:
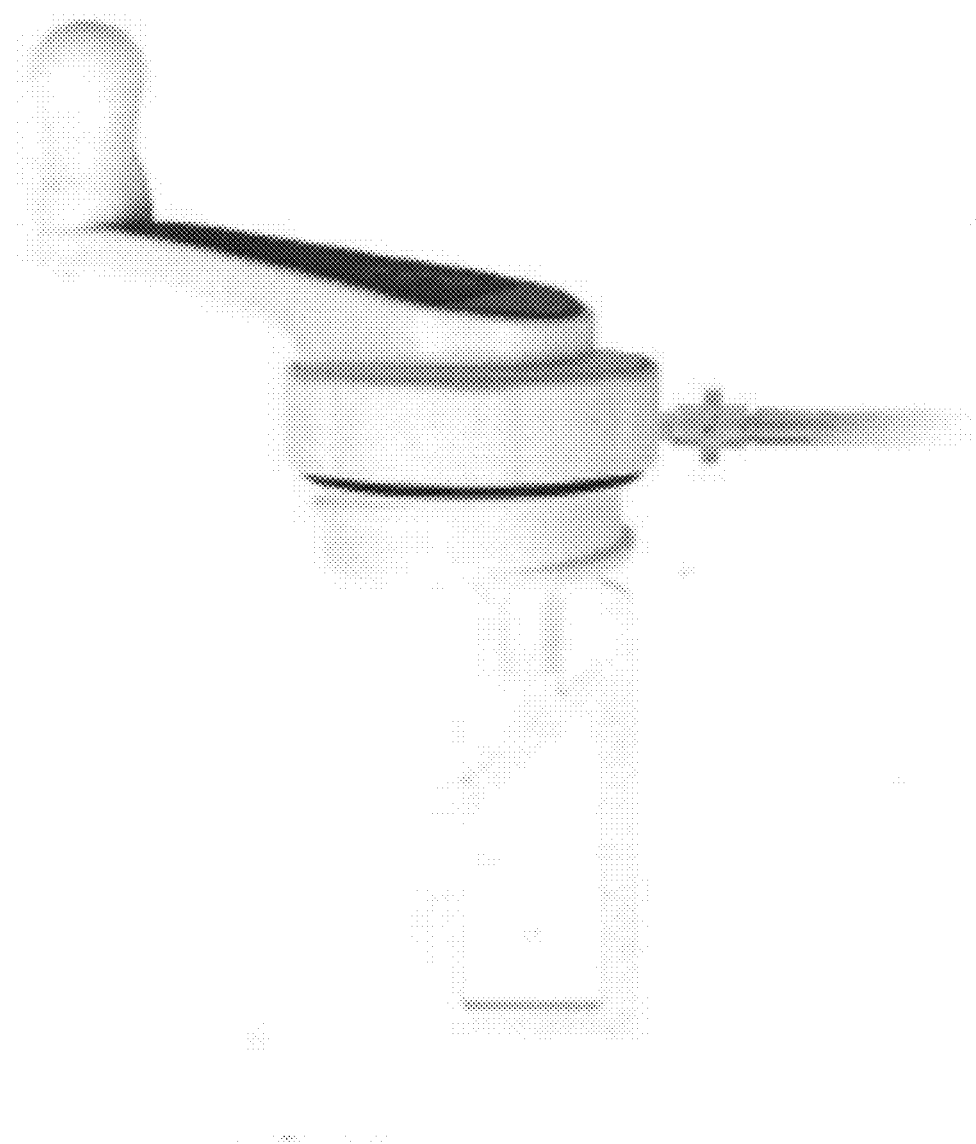
FIG. 5 is a photograph of a lid being connected to a vacuum system using a vacuum tube in accordance with one embodiment of a method of the present invention.

2. Connect vacuum system to Lid using vacuum tube (see FIG. 5).

3. Pour powder into cement base first. Add monomer when ready and begin mixing cement immediately. Mix for 45 seconds. Do not allow powder and monomer to sit for any length of time before mixing, as time is critical in the LiquiFlo™ cementing procedure. Note: Do not mix vigorously.

4. Once mix is complete, pull the vacuum tube from the mixer lid before proceeding to the next step.

IV. Syringe Transfer

Figure 6:
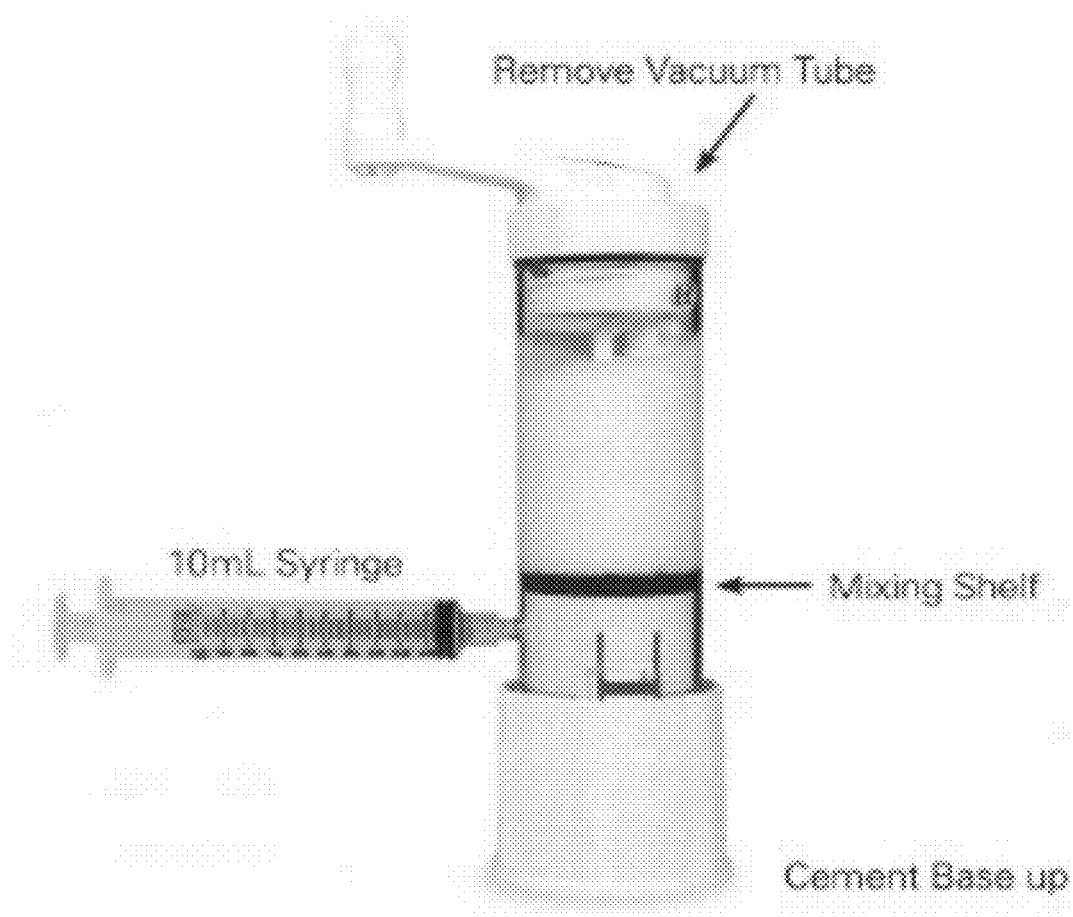
FIG. 6 is a photograph of one view of a standard 10 mL syringe connected to a lure adapter on the side of a mix system suitable for use in one embodiment of a method of the present invention.

Syringe transfer can be performed according to the following steps (without limitation):

1. Connect a standard 10 mL syringe to the lure adapter on the side of the mix system (see FIG. 6). Once connected, twist the bottom of the cement base so that the bottom of the cement mixing shelf lowers, and allows cement to flow through the port.

Figure 7:
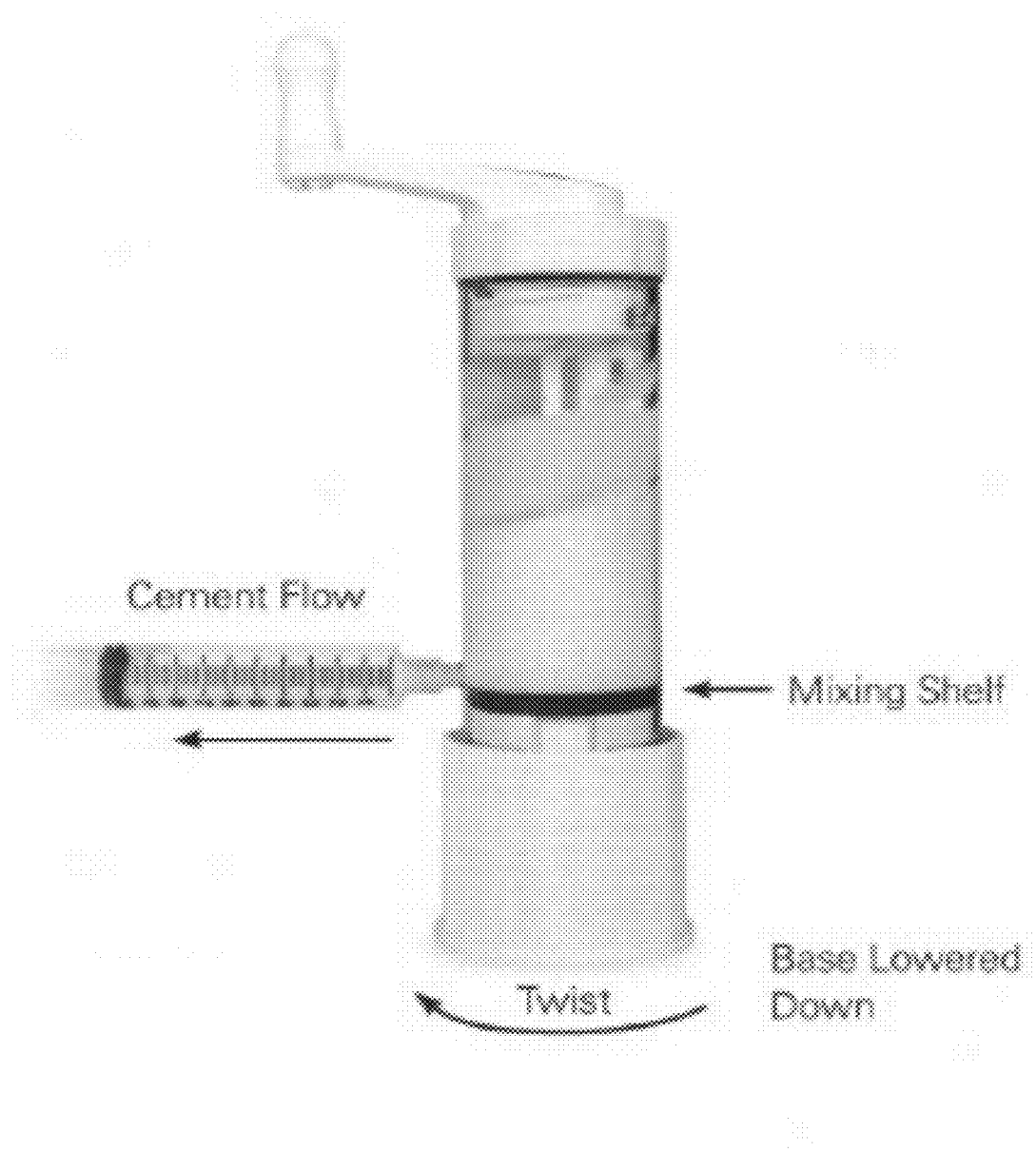
FIG. 7 is a photograph of one view of a standard 10 mL syringe connected to a lure adapter on the side of a mix system suitable for use in one embodiment of a method of the present invention. This view demonstrates that pulling the plunger on the syringe will allow the syringe to become filled with the cement.

2. Pull the plunger on the syringe to 10 mL (see FIG. 7). Cement will follow the plunger and fill the syringe. Do not pull further than the 10 mL mark, as this can disengage the plunger. Complete for all four (4) syringes.

Figure 8:
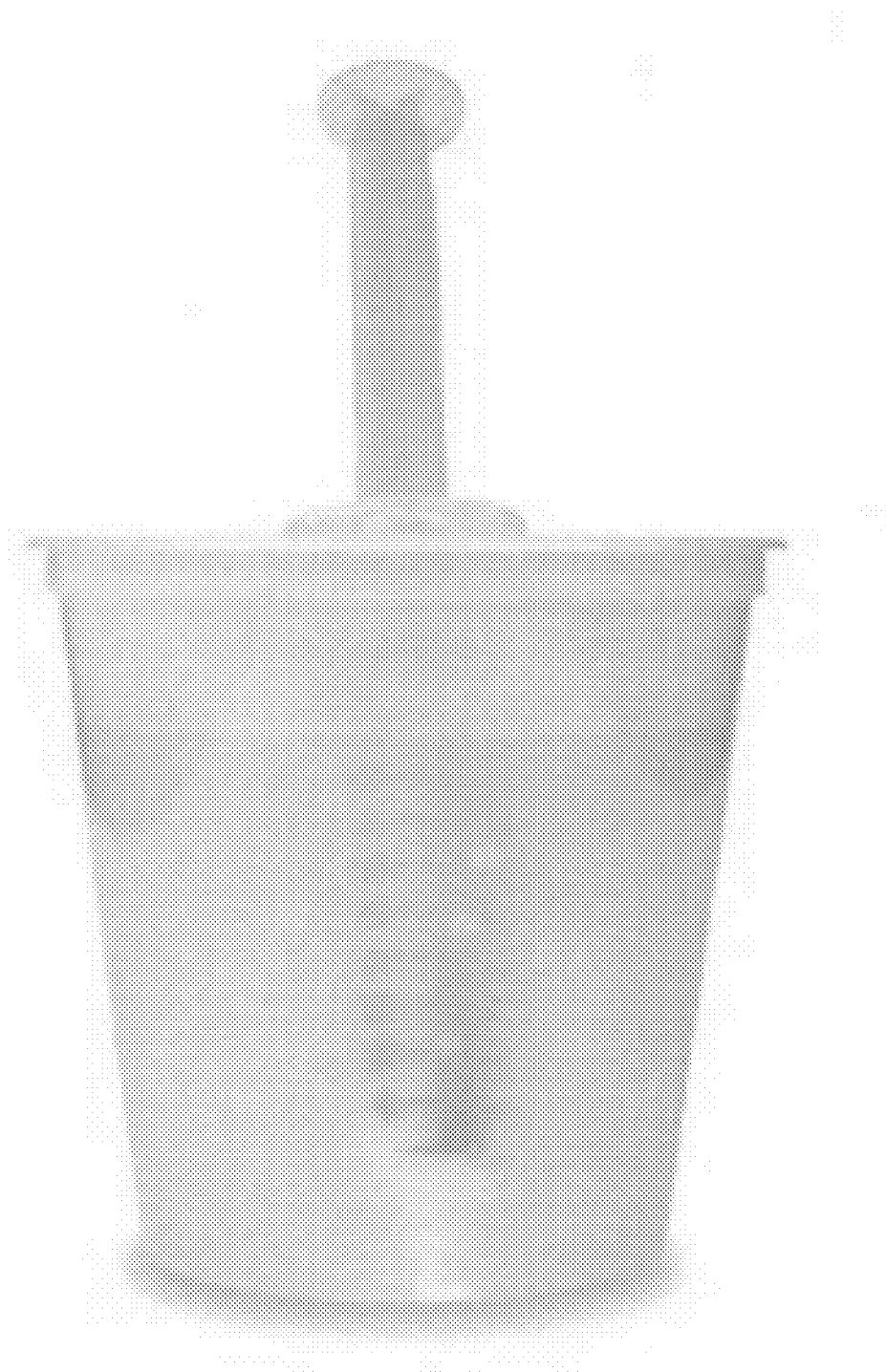
FIG. 8 is a photograph of one view of a standard 10 mL syringe in a chilled saline bath in accordance with one embodiment of a method of the present invention.

3. Once the four (4) syringes are full, complete the "Drip Test" with one of the syringes, then place one (1) syringe in chilled saline bath and give surgeon one (1) full 10 mL syringe (see FIG. 8).

V. Viscosity Drip Test

A viscosity drip test can be performed according to the following steps (without limitation):

1. This syringe gauges the cement viscosity through the drip test. Hold the syringe vertically, and allow cement to freely drip from the luer nozzle.

Figure 9:
FIG. 9 is a photograph of one view of a standard 10 mL syringe being held for monitoring of drip rate or flow of cement from the syringe during one embodiment of a viscosity drip test in accordance with one embodiment of a method of the present invention.

2. Monitor the drip rate or flow of the cement from the 10 mL. syringe with no plunger installed as shown in FIG. 9.

3. Flow of cement will turn to a perceptible dripping rate. When drip rate approaches 1 drip per second the surgeon may begin injection of the third syringe into the tibial implant.

4. If the surgeon is not ready for the femoral syringe within the allocated time, use the 1st syringe chilled in saline bath.

VI. Cement Injection

Cement injection for the tibia and femur can be performed as described below, without limitation. Cement curing can also be performed as described below, without limitation.

Tibia: Surgeon will use one syringe to inject cement into the tibial implant. Tibial implant requires a 45 degree injector and will require approximately 3 cc of cement injected.

Femur: Once the tibial implant is cemented, surgeon will inject the femoral implant with the 130 degree injector attached into the cement portals. Note: Do not impact implant prior to injection. Inject 5-7 cc of cement into the femoral implant, then impact femoral implant to seat implant into resected bone. Remove any extruded cement from femoral and tibial areas.

Cement Curing: Let cement cure for at least 15 minutes. To expedite curing process, warm sterile saline (cardiac) can be introduced throughout the incision site. Flex knee and visualize implants for any additional extruded cement and remove if present.

EXAMPLES

The following examples are intended to illustrate particular embodiments of the present invention, but are by no means intended to limit the scope of the present invention.

Example 1

The Effect of Chilling PMMA Bone Cement Polymerization to Prolong Injectability

Summary

When mixed, polymethylmethacrylate (PMMA) bone cement undergoes an irreversible reaction, eventually hardening into a solid state. The rate of this reaction is largely dependent on the temperature of the components involved.

Different states of the cement are identified as the reaction progresses, defined by the apparent viscosity of the cement. Since the speed of the reaction is dependent on temperature, the time that the cement remains in a desirable state can be prolonged by artificially decreasing the temperature. In order to more closely study the effect of chilling the cement to prolong the previously defined "injectability" state this series of tests was carried out to appropriately define a protocol and limitations regarding chilling cement in a clinical situation.

The objectives of this study are to define a limit, if any, to the effectiveness of using an ice bath to limit the progression of the reaction of curing PMMA cement and extend the amount of time it is considered to be injectable.

Introduction

This cement chilling study was conducted at the VOT Solutions laboratory in Warsaw, Ind.

Different states of the PMMA cement are identified as the reaction progresses, defined by the apparent viscosity of the cement. Since the speed of the reaction is dependent on temperature of the components involved, the time that the cement remains in a desirable state can be prolonged by artificially decreasing the temperature of those components. In order to more closely study the effect of chilling the cement to prolong the previously defined "injectability" state this series of tests was determined necessary to appropriately define a protocol and limitations regarding chilling cement in a clinical situation.

The objectives of this study are to define a limit, if any, to the effectiveness of using an ice bath to limit the progression of the reaction of curing PMMA cement and extend the amount of time it is considered to be injectable.

Materials and Methods

The same test setup from TM0310-002 "Injectability as measured viscosity" was used, and the protocol developed to determine viscosity was also used from that document, as well as the definition of injectability (as being less than 2500 cP).

An "ice bath" for the purposes of this study is defined as a large container first filled with ice, then cold water. The temperature of all ice baths used was measured to be around 32 degrees F., which is expected in a mixture of a large combination of ice and cold water. Both ice and water were still present in the container when in use for all test cases.

An ice bath was chosen as the method to lower the temperature in this study primarily because it is an easy system to recreate in any operating room. Also, placing nearly anything in near-freezing water combined with ice is a fast, efficient way to conduct heat away and lower its temperature because of the combined effects of the heat buffer of the ice and the increased contact area given by the liquid nature of the water.

All volumes used were contained in 10 cc syringes to both control bolus effect variables and to be more clinically relevant. The temperature of the room was controlled to be 60 degrees F. for all test cases.

In all cases the syringe was submerged completely into the ice bath after a 1 Hz drip test.

| Supplies | | |
|---|---|---|
| Product | Manufacturer | Components Used |
| 10 cc Syringes | Becton Dickinson and Co. | 16 |
| Cement mixer | Summit | 3 |
| MLP-1K-CO Load Cell | Omegadyne | 1 |
| Displacement Detector | — | 1 |
| DP25-E Process Filter | Omega Inc | 1 |
| PMD-1208FS DAQ board | Measurement Computing | 1 |
| LabTech Software system | LabTech Software LLC | 1 |
| Palacos LV Cement | Heraeus | 3 |

Results

Figure 10:
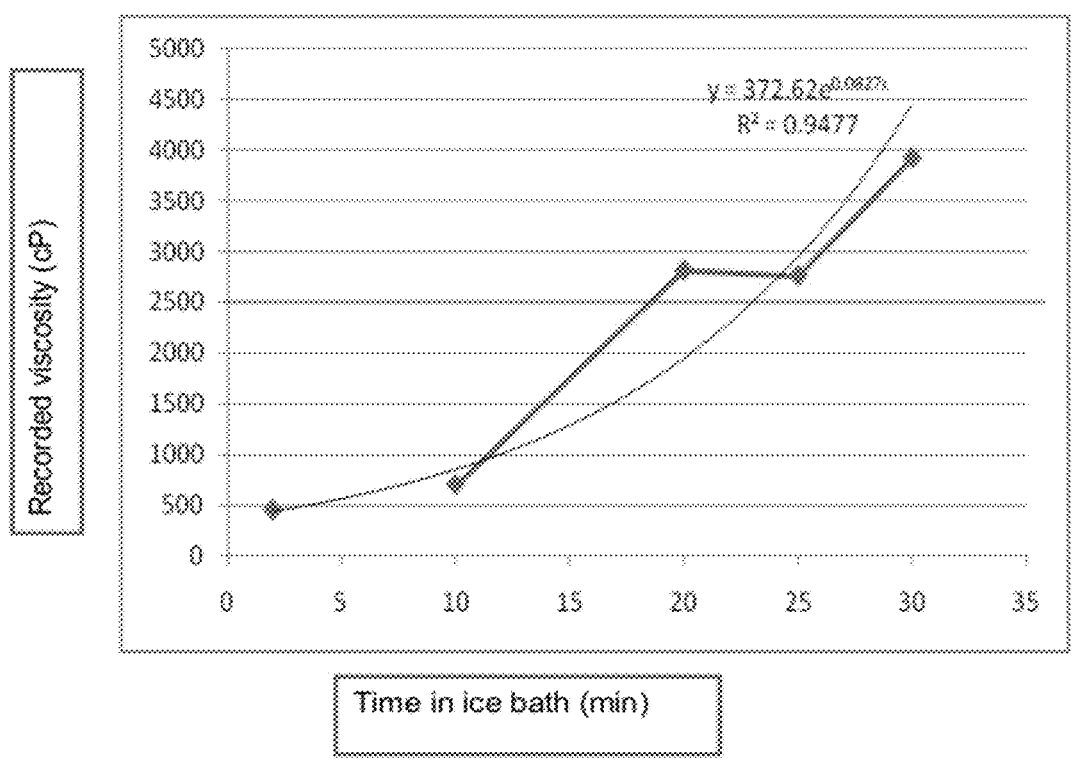
FIG. 10 is a graph showing the results of an experiment to test the effect of chilling PMMA bone cement polymerization to prolong injectability. The graph shows recorded viscosity (cP) over a period of time in an ice bath (minutes) for a PMMA bone cement polymerization reaction.

Looking at the data in FIG. 10 one can see that the reaction certainly still progresses after placement in an ice bath—just at a slower pace.

Using viscosity measurements at time points at 2 min, 5 min (which had to be excluded), 10 min, 20 min, 25 min, 30 min, and 45 min (which also had to be excluded) we were able to create this approximation of the rate progression in the ice bath.

The 5 min point had to be excluded because there was no point in, time where the load was even at 10 lbs so the resulting plunger velocity was meaningless.

The 45 min point was excluded as the reaction had progressed beyond the point where 10 lbs was enough force to get any movement at all from the plunger on the syringe. At this point the cement was clearly in "setting" phase, with more plastic solid properties than viscous liquid properties.

Discussion

The data showed that the cement reaches the injectability limit of 2500 cP around 20 minutes, though there is significant deviance from the predictive line. Since the fit of the trend line is not ideal, to prevent leaving the syringe in too long (taking into consideration different OR temperatures and situation would all create different results) we want a factor of safety and estimate lower. 15 minutes is a good upper limit to the time any post drip-test syringe should remain in the ice bath and expect to be used.

These results do not include allowances for ambient temperature, as most effects of ambient temperature are removed shortly after the syringe is placed into the ice bath, and since all syringes are placed in the bath at the same state (post drip-test) there should be little carry-over effects. Residual higher temperatures within the cement and syringe could lead to shorter times in theory, however, and this is all the more reason to decrease the recommended icing time for expected use from about 20 minutes to 15 minutes.

It is important to remember that these syringes had reached the 1 Hz drip-test state immediately before being placed within the ice bath. There remains the option to place the syringe in the ice bath before this injectability milestone is reached, and this should increase the injectability even further. Since the tested reactions had at least a couple of minutes to progress in ambient temperature, the injectability window certainly increases even further when placed in the bath before the drip test mark.

CONCLUSIONS

Based off the results of this test, we recommend placing a syringe in a pre-prepared ice bath as described when or before the drip test reaches 1 Hz. This syringe can be expected to remain injectable for up to 15 minutes, well past any syringes of cement left out of the ice bath. This syringe may or may not need to be used in the surgery, but that it can remain as a backup will doubtless be helpful in case the cementing step takes longer than normal or if the ambient temperature causes the other extra syringes to be too viscous too quickly for use. This will prevent another mix from being needed (which would increase the overall time of the procedure).

Since the period of time between needing the first syringe and any other syringe of cement in a given procedure is usually well under 10 minutes, but possibly at times up to 10 minutes, this is a good procedural recommendation that is both easy to execute and easy to remember.

REFERENCES

Citation of a reference herein shall not be construed as an admission that such reference is prior art to the present invention. All references cited herein are hereby incorporated by reference in their entirety. Below is a listing of various references cited herein:
1. Parks M L, Walsh H A, Salvati E A, Li S. Effect of increasing temperature on the properties of four bone cements. *Clin Orthop* 1998; 355:238-248
2. Chavali R, Resijek R, et. Al. Extending Polymerization Time of Polymethylmethacrylate Cement in Percutaneous Vertebroplasty with Ice Bath Cooling. *AJNR Am J Neuroradiol* 2003; 24:545-546
3. Lidgren L, Bodelind B, Moller J, Bone cement improved by vacuum mixing and chilling. *Acta Orthop.Scand* 1987; 57:27-32
4. Pearson G P, Jones D F, Wright V. Letter. Effect of operating theatre temperatures on the setting times of acrylic cements for use in orthopaedic surgery. *Lancet* 1975; 2:184

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of implanting a prosthesis device in a subject, said method comprising:
    providing a prosthesis device to be attached to an exposed surface of a bone of a subject;
    conducting a viscosity test on a bone cement to determine a viscosity range at which the bone cement is in liquid form suitable for applying to a bone-implant interface region, wherein said bone-implant interface region comprises a region between the exposed surface of the bone and an outer surface of the prosthesis device, wherein said viscosity test comprises a drip test effective to measure the rate of flow, wherein the viscosity test is suitable to provide a beginning and ending point for applying the bone cement in liquid form, wherein said drip test is conducted in a standard 10 mL syringe at ambient room temperature;
    applying the bone cement in liquid form to the bone-implant interface region;
    contacting the bone cement to both the exposed surface of the bone and the outer surface of the prosthesis device under conditions effective to allow the bone cement to cure; and
    after said applying step and/or after said contacting step, subjecting the bone cement to curing conditions effective to decrease the setting time of the implanted prosthesis device,
    thereby resulting in attachment of the prosthesis device to the bone of the subject.

2. The method according to claim 1, wherein the prosthesis device is a joint prosthesis device for replacing or partially replacing a joint selected from the group consisting of a knee, a hip, a shoulder, an ankle, an elbow, a spinal disc, a cervical disc, and a small joint.

3. The method according to claim 2, wherein the joint prosthesis device is for a partial knee replacement, a patellofemoral replacement, or a total knee replacement.

4. The method according to claim 2, wherein the small joint is selected from the group consisting of a PIP joint (finger), an MCP joint (knuckle), a DIP joint (finger), a CMC joint (thumb), and a metatarsophalangeal joint (toe).

5. The method according to claim 1, wherein the prosthesis device is selected from the group consisting of a tibial component, a femoral component, a patellar component, an acetabular component, a glenoid component, a humeral component, a talar component, an ulnar component, and a fusion cage component.

6. The method according to claim 1, wherein the prosthesis device comprises a body having at least one port through which the bone cement in liquid form is applied to the bone-implant interface region.

7. The method according to claim 6, wherein said applying step comprises introducing the bone cement in liquid form to the bone-implant interface region through the at least one port of the prosthesis device.

8. The method according to claim 1, wherein the bone cement in liquid form comprises poly(methyl methacrylate) (PMMA) at a viscosity selected from the group consisting of about 10,000 centipoise (cP) or less, about 9,000 cP or less, about 8,000 cP or less, about 7,000 cP or less, about 5,000 cP or less, about 4,000 cP or less, about 3,000 cP or less, about 2,500 cP or less, about 2000 cP or less, about 1500 cP or less, about 1000 cP or less, about 500 cP or less, and about 250 cP or less, wherein said viscosity is determined in accordance with the Hagen-Poiseuille equation.

9. The method according to claim 1, wherein the beginning point comprises a rate of flow selected from the group consisting of 2 drips/second, 1 drip/second, and 1 drip/5 seconds, and the like.

10. The method according to claim 1, wherein the ending point comprises a rate of flow of selected from the group consisting of less than about 1 drip/5 seconds, less than about 1 drip/10 seconds, and no apparent drips/5-10 seconds.

11. The method according to claim 1, wherein said drip test further comprises measuring migration of the bone cement on a test surface under conditions effective to determine when the bone cement is in a liquid form having a suitable viscosity range for said applying step.

12. The method according to claim 1, wherein said drip test further comprises measuring the change in temperature of the bone cement under conditions effective to determine when the bone cement is in a liquid form having a suitable viscosity range for said applying step.

13. The method according to claim 1, wherein said subjecting comprises adding heat to the bone cement.

14. The method according to claim 13, wherein the heat is added using saline at a temperature of between about 80 and 100 degrees F.

15. The method according to claim 1, wherein the bone cement in liquid form is applied to the bone-implant interface region using a delivery instrument.

16. The method according to claim 15, wherein an injector adapter is used to facilitate application of the bone cement in liquid form from the delivery instrument to the bone-implant interface region.

17. The method according to claim 16, wherein the prosthesis device comprises a body having at least one port through which the bone cement in liquid form is applied to the bone-implant interface region, and wherein the injector adapter is configured to couple the injection instrument to the at least one port of the prosthesis device.

18. The method according to claim 15, wherein the injection instrument is a syringe.

19. The method according to claim 18, wherein the syringe is configured to contain a volume of liquid of up to about 50 cubic centimeters (cc).

20. The method according to claim 1 further comprising:
prior to and/or during said applying step, delaying curing of the bone cement from its liquid form to its cured form.

21. The method according to claim 20, wherein said delaying comprises maintaining the bone cement in liquid form at a temperature range selected from the group consisting of between about 0° F. and about 40° F., between about 10° F. and about 40° F., between about 15° F. and about 40° F., between about 20° F. and about 40° F., between about 25° F. and about 40° F., between about 30° F. and about 38° F., and between about 32° F. and about 35° F.

22. The method according to claim 20, wherein said delaying comprises maintaining the bone cement at a temperature of not warmer than about 0° F.

23. The method according to claim 20, wherein said delaying comprises maintaining the bone cement in crushed ice, a mixture of ice and water, refrigerator-chilled saline, and/or freezer-chilled saline.

24. The method according to claim 23, wherein said maintaining comprises incubating the bone cement in liquid form in an ice bath or chilling the bone cement in liquid form using chilled saline.

25. The method according to claim 24, wherein said incubating is for a period of not more than about 25 minutes and/or not more than between about 10 and about 25 minutes prior to applying the bone cement in liquid form to the bone-implant interface region.

* * * * *